US010656101B2

(12) United States Patent
Tognina et al.

(10) Patent No.: US 10,656,101 B2
(45) Date of Patent: May 19, 2020

(54) CONFIGURING A PORTABLE X-RAY DETECTOR FOR USE WITH AN IMAGE ACQUISITION WORKSTATION BASED ON COLOR DETECTION

(71) Applicant: VAREX IMAGING CORPORATION, Salt Lake City, UT (US)

(72) Inventors: Carlo Tognina, Stanford, CA (US); Rudiger Schwartz, Sunnyvale, CA (US); Cesar Proano, Palo Alto, CA (US); Keith Gray, San Ramon, CA (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 288 days.

(21) Appl. No.: 15/719,591

(22) Filed: Sep. 29, 2017

(65) Prior Publication Data

US 2019/0101495 A1 Apr. 4, 2019

(51) Int. Cl.
*G01N 23/04* (2018.01)
*A61B 6/00* (2006.01)
*A61B 90/94* (2016.01)

(52) U.S. Cl.
CPC ........... *G01N 23/04* (2013.01); *A61B 6/4233* (2013.01); *A61B 6/4494* (2013.01); *A61B 6/54* (2013.01); *A61B 6/563* (2013.01); *A61B 90/94* (2016.02); *A61B 6/545* (2013.01); *A61B 6/585* (2013.01); *G01N 2223/306* (2013.01); *G01N 2223/42* (2013.01)

(58) Field of Classification Search
CPC ..... A61B 6/545; A61B 6/4283; A61B 6/4494; A61B 90/94; A61B 90/90; A61B 90/92
See application file for complete search history.

(56) References Cited

U.S. PATENT DOCUMENTS

| 9,526,465 | B2* | 12/2016 | Nenoki | A61B 6/4283 |
| 2009/0130983 | A1* | 5/2009 | Venturino | A61B 6/00 455/66.1 |
| 2012/0207278 | A1* | 8/2012 | Yonekawa | A61B 6/4233 378/98.5 |
| 2012/0286167 | A1* | 11/2012 | Eguchi | A61B 6/00 250/393 |

* cited by examiner

*Primary Examiner* — Yara B Green
(74) *Attorney, Agent, or Firm* — Su IP Consulting

(57) ABSTRACT

An X-ray imaging device includes a color sensor configured to generate a color signal indicating a particular color sensed, an imaging matrix of pixel detector elements that are each configured to detect photon energy and generate an image signal, and a controller that is coupled to the color sensor, the imaging matrix, and the wireless transceiver. The controller is configured to receive a color signal from the color sensor, determine an identifier of the computing device external to the X-ray imaging device based on the color signal, and change at least one operational setting of the X-ray imaging device based on the identifier.

20 Claims, 5 Drawing Sheets

CONFIGURING A PORTABLE X-RAY DETECTOR FOR USE WITH AN IMAGE ACQUISITION WORKSTATION BASED ON COLOR DETECTION

BACKGROUND

Unless otherwise indicated herein, the approaches described in this section are not prior art to the claims in this application and are not admitted to be prior art by inclusion in this section.

Digital radiography is a form of X-ray imaging in which digital X-ray sensors are used to generate digital images, and has multiple advantages over traditional film-based techniques. By bypassing chemical processing, digital radiography is more time efficient, provides digital images for immediate image preview, facilitates image enhancement, and generally requires less radiation to produce an image of similar contrast.

Digital radiography is now used in many applications, including medical diagnostics, veterinary care, dental imaging, industrial inspection, and security. Each of these applications can benefit from a fully portable flat panel X-ray sensor that is not physically tethered to the associated workstation or computer that receives acquired images, performs image processing and enhancement, and provides a user interface for controlling image acquisition. Consequently, flat panel X-ray sensors have been developed with a form factor that can be manually positioned for X-ray image acquisition and easily carried between different workstations. In addition, some flat panel X-ray sensors are configured for wireless communication with the associated workstation for transferring image data to the workstation and receiving control inputs from the workstation. Thus, during normal use, such flat panel X-ray sensors are not physically coupled to an external workstation or computer.

SUMMARY

In accordance with at least some embodiments of the present disclosure, an X-ray imaging device comprises a color sensor configured to generate a color signal indicating a particular color; an imaging matrix of pixel detector elements that are each configured to detect photon energy and generate an image signal; a wireless transceiver configured to transmit image data to a computing device external to the X-ray imaging device; and a controller that is coupled to the color sensor, the imaging matrix, and the wireless transceiver. The controller is configured to receive an activation input; in response to receiving the activation input, activating the color sensor; receive a color signal from the color sensor; determine an identifier of the computing device external to the X-ray imaging device based on the color signal; cause the wireless transceiver to establish a wireless communication connection with the computing device external to the X-ray imaging device based on the identifier; and change at least one operational setting of the X-ray imaging device based on the identifier.

In accordance with at least some embodiments of the present disclosure, a method of configuring an X-ray imaging device for use with a computing device external to the X-ray imaging device computing comprises receiving an activation input; in response to receiving the activation input, activating a color sensor configured to generate a color signal indicating a particular color; receiving the color signal from the color sensor; determining an identifier of the computing device external to the X-ray imaging device based on the color signal; causing a wireless transceiver included in an X-ray imaging device to establish a wireless communication connection with the computing device external to the X-ray imaging device based on the identifier, and changing at least one operational setting of the X-ray imaging device based on the identifier.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
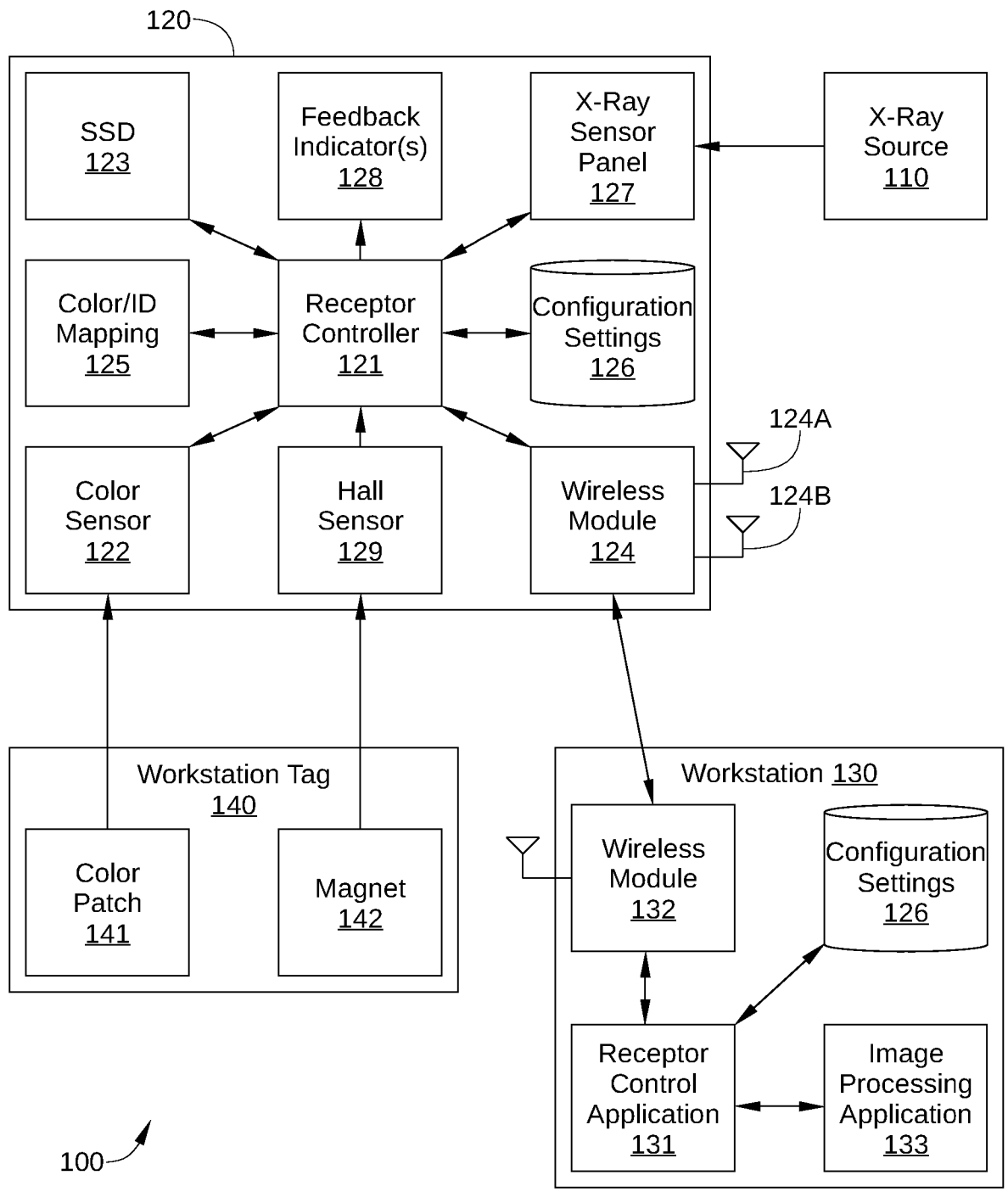
FIG. 1 is a block diagram of a digital radiographic system, according to one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

In applications of digital radiography in which a single flat panel X-ray sensor is shared between multiple image acquisition workstations, such as in a hospital environment, the flat panel X-ray sensor must be reconfigured whenever moved to a new workstation. For example, wireless communication settings in the flat panel X-ray sensor need to be updated so that wireless communications can be established with the new workstation. In addition, software settings of applications running on the new workstation may also require updating, including image acquisition settings (portrait vs. landscape, X-ray dose, etc.), enabling or disabling certain features of the flat panel X-ray sensor, and the like. Because conventional wireless communication is not yet established with the new workstation, such as a WiFi connection, reconfiguring the flat panel X-ray sensor to the new workstation must be performed by other means.

It is common practice to reconfigure a flat panel X-ray sensor for a new workstation by directly connecting via a cable. However, this approach suffers from significant drawbacks. For example, the cable creates a trip hazard when in use, can be lost or damaged, and generally undergoes some mechanical and/or electrical deterioration with each insertion or removal. Thus, there are multiple reliability concerns associated with reliance on such a reconfiguration cable. In addition, the ability of any device with a cable interface port, such as a universal serial bus (USB) port, to conform to certain solid and liquid ingress protection standards is problematic. For example, a flat panel X-ray sensor employed in a clinical environment may be expected to conform to the IP56 code, i.e., possessing dust-protection and the ability to withstand jets of liquid, and an IP56-compliant USB port can introduce significant cost and reliability issues.

Alternatively, near-field communications (NFC) between the flat panel X-ray sensor and the new workstation can be employed for reconfiguring a flat panel X-ray sensor. For example, an NFC reader incorporated in the flat panel X-ray sensor can be used to read configuration information from an NFC tag associated with a particular workstation. Drawbacks to such an approach include the need for additional devices for programming each NFC tag, the additional software implementation in both the flat panel X-ray sensor and the workstation to support such communication, the high power consumption of the NFC reader incorporated into the flat panel X-ray sensor, the high cost of certification for devices using NFC, and the high potential for damage to each NFC tag.

Alternatively, a flat panel X-ray sensor can be equipped with a laser bar code reader, and configuration information can be read from a bar code tag associated with a particular workstation. Drawbacks to such an approach include the high power consumption, high cost, and prohibitive size of a laser bar code reader, the additional software implementation in the flat panel X-ray sensor to support the laser bar code reader, and the degradation in laser reliability over time.

Yet another alternative for reconfiguring a flat panel X-ray sensor for a new workstation is to incorporate either a display screen and input buttons or a touch-sensitive screen into the flat panel X-ray sensor. However, scrolling through a small screen can be time-consuming and counterintuitive, and the screen itself greatly reduces the durability of the sensor. Furthermore, mechanical input buttons degrade with time and use, add cost, and generally make conformance to solid and liquid ingress protection standards more difficult.

In light of the above, there is a need in the art for devices, systems, and methods to configure an imaging device, such as an X-ray sensor, to a particular workstation or other computing device.

According to various embodiments of the present disclosure, an X-ray flat-panel detector that is shared between multiple image acquisition workstations can be configured with settings appropriate for a selected workstation from the multiple image acquisition workstations. Specifically, a color sensor incorporated into the X-ray flat-panel detector is activated and then used to detect the color of a color-coded identification tag associated with the selected workstation. Based on the detected color, the X-ray flat-panel detector then changes one or more operational settings of the X-ray flat-panel detector, thereby enabling X-ray image acquisition via the selected workstation without inputs or other configuration changes being entered by the user. The operational settings may include settings that enable wireless communication with the particular workstation, such as the service set identifier (SSID), channel, and/or frequency of the workstation. Additionally, the operational settings may include default imaging settings (such as image orientation, i.e., portrait/landscape) and/or enablement/disablement of certain operating features of the workstation, such as an auto sleep function, auto wake upon detection of X-rays, and the like. In some embodiments, the color sensor is activated in response to a Hall detector sensing a magnet included with the color-coded identification tag.

FIG. 1 is a block diagram of a digital radiographic system 100, according to one or more embodiments of the present disclosure. Digital radiographic system 100 is configured to generate a digital X-ray image, and includes an X-ray source 110, an X-ray detector 120, a workstation 130, and a workstation tag 140. Digital radiographic system 100 generates a digital X-ray image when X-ray photons, generated by X-ray source 110, pass through a patient, sample, or other object, and are incident on X-ray detector 120. As X-ray photons pass through the object of interest, internal structures of the object cause spatial variations in the intensity of X-ray photons actually incident on X-ray detector 120. In indirect detection, X-ray detector 120 converts the incident X-ray photons to visible or other light photons via a scintillator, and a photodiode layer generates a digital output signal based on the light photons. The digital output signal can then be transmitted wirelessly to workstation 130 for subsequent image processing, analysis, and storage. As described herein, workstation tag 140 is employed to enable the configuring of X-ray detector 120 for use with workstation 130. Thus, workstation tag 140 enables wireless communication between X-ray detector 120 and workstation 130, and the programming of one or more operational settings of X-ray detector 120.

X-ray source 110 can be any suitable X-ray source for emitting X-ray photons, such as an X-ray tube (or tube generator). Generally, X-ray source 110 is controlled by workstation 130 or other computing device, via a wired or wireless connection. Specifically, workstation 130 enables selection of X-ray attributes suitable for a specific image acquisition or acquisition session. For example, workstation 130 can control the power supply of X-ray source 110, thereby producing a desired peak kilovoltage (kVp), current, and duration of exposure.

X-ray detector 120 is an X-ray imaging device that is typically battery powered and operable to be communicatively connected to workstation 130. To that end, X-ray detector 120 includes a controller 121, a color sensor 122, a solid-state drive (SSD) 123 or other non-volatile data storage medium, a wireless module 124, a color/ID mapping 125, one or more configuration settings 126, an X-ray sensor panel 127, and, in some embodiments, one or more feedback indicators 128 and/or a Hall effect sensor 129.

Controller 121 may be any suitable processor implemented as a central processing unit (CPU), an application-specific integrated circuit (ASIC), a field programmable gate array (FPGA), any other type of processing unit, or a combination of different processing units. In general, controller 121 may be any technically feasible hardware unit capable of processing data, controlling the image acquisition hardware of X-ray detector 120, and reconfiguring X-ray detector 120 for use with a specific workstation 130. Thus, controller 121 is configured to receive signals from the readout electronics of X-ray sensor panel 127, generate a digital representation of an x-ray image based on the received signals, and transmit the digital representation to a selected workstation 130 for image processing. In addition, controller 121 is configured to receive an activation input, in response to receiving the activation input, activate a color sensor, receive a color signal from the color sensor, determine an identifier of a particular workstation 130 based on the color signal, cause wireless module 124 to establish a wireless communication connection with the particular workstation 130 based on the identifier, and change at least one operational setting of X-ray detector 120 based on the identifier. In some embodiments, controller 121 is an FPGA that includes image acquisition firmware 101 and reconfigure firmware 102. Alternatively, controller 121 can be a CPU that executes an image acquisition application (not shown) and a reconfigure application (not shown) residing in a volatile memory (not shown). Image acquisition firmware 101 includes logic for controlling the image acquisition hardware of X-ray detector 120, and reconfigure firmware 102 includes logic for reconfiguring X-ray detector 120 for use with a specific workstation 130.

When activated, color sensor 122 is configured to digitally measure red-green-blue (RGB) and, in some embodiments, white information, and output the measured RGB and white information as a color signal to controller 121. For example, in some embodiments, color sensor 122 includes a red-sensitive photodiode, a green-sensitive photodiode, a blue-sensitive photodiode, and, in some embodiments, a white-sensitive photodiode. Alternatively, color sensor 122 can include any other technically feasible collection of color-sensitive photodiodes that together can be employed to digitally measure the color of a color patch 141 included on workstation tag 140 (described below). In some embodiments, color sensor 122 also includes a white light source that illuminates color patch 141 with a relatively uniform spectrum of visible light wavelengths, thereby enhancing the accuracy of color measurements performed by color sensor 122.

Wireless module 124 may be any technically feasible wireless chip, card, or other device that enables X-ray detector 120 to communicate wirelessly with workstation 130 in FIG. 1 and/or with other workstations 130 not shown in FIG. 1. Examples of devices suitable for use as wireless module 124 include a Wifi module, a wireless local area network (WLAN) module, a 3rd Generation Partnership Project (3GPP) module, and the like. For example, in some embodiments, wireless module 124 is an Institute of Electrical and Electronics Engineers (IEEE) 802.11ac/n device capable of providing a WiFi Direct connection to workstation 130. Alternatively or additionally, in some embodiments, wireless module 124 is a device capable of providing a Bluetooth connection to user access device 110. Thus, in some embodiments, wireless module 124 includes two antennas 124A and 124B, and is capable of both WiFi and Bluetooth operation simultaneously.

Color/ID mapping 125 includes data indicating a one-to-one mapping of specific colors to different workstations 130. As a result, for a scenario in which X-ray detector 120 is shared between multiple workstations 130, a unique color is mapped or otherwise associated with each such workstation 130. Thus, each workstation 130 is associated with a single unique color in color/ID mapping 125.

In some embodiments, a large number of workstations 130 share use of X-ray detector 120, for example 10, 20, or more, and the number of workstations 130 sharing X-ray detector 120 can exceed the number unique colors that can be distinguished by color sensor 122. In such embodiments, color/ID mapping 125 can include a mapping of unique color groups to each of the workstations 130 sharing X-ray detector 120, rather than a mapping of individual colors to each of the workstations 130. Consequently, a large number of workstations 130 can be uniquely identified via color sensor 122, even when color sensor 122 can only distinguish between a relatively small number of different colors, e.g., eight. To wit, when color sensor 122 can distinguish between N different colors, and each color group includes M colors in series, the number of different workstations 130 that can be uniquely identified by color group and color sensor 122 is $N^M$.

Configuration settings 126 include operational settings for X-ray detector 120 and/or software settings associated with the control or operation of X-ray detector 120. For example, in some embodiments, workstation configuration settings 126 include one or more wireless communication settings for some or all workstations 130 that share X-ray detector 120, such as the respective SSID, channel, and/or communication frequency of some or all such workstations 130. In some embodiments, workstation configuration settings 126 include default imaging settings (such as image orientation) and/or one or more software settings for an application that runs on workstations 130 and controls operation of X-ray detector 120 (such as a receptor control application 131). For example, workstation configuration settings 126 may include settings such as peak kilovoltage (kVp), current, and duration of exposure employed during X-ray image acquisition, idle time between image acquisitions before X-ray detector 120 enters sleep mode, etc. In some embodiments, workstation configuration settings 126 include settings indicating the enablement or disablement of an operating feature of X-ray detector 120, such as an auto sleep mode, an auto wake upon detection of X-rays, automatic calibration processes, and the like. Because some or all of the above settings are stored locally in X-ray detector 120 as workstation configuration settings 126, such workstation-specific information does not need to be entered by a user whenever X-ray detector 120 is employed with a different workstation 130. Instead, as described herein, whenever X-ray detector 120 is relocated to a different workstation 130, X-ray detector 120 can automatically reconfigure one or more operational settings, and/or cause operational settings stored in a particular workstation 130 to be updated.

In the embodiment illustrated in FIG. 1, workstation configuration settings 126 are depicted being stored locally in X-ray detector 120, for example in SSD 123 or some other non-volatile data storage medium. Alternatively or additionally, in some embodiments, workstation configuration settings 126 are stored in workstation 130. Thus, once X-ray detector 120 initiates wireless communication with a particular workstation 130, that particular workstation 130 can control X-ray detector 120 using the appropriate operational settings for X-ray detector 120.

X-ray sensor panel 127 includes a matrix or array of pixel detector elements that each converts incident X-ray photons to electrical charge. In embodiments in which X-ray detector 120 is configured as an indirect flat panel detector, a scintillator material in X-ray detector 120 is excited by incident X-rays and emits light, which is detected by a plurality of photodiodes. Each diode generates a signal (e.g., a voltage that is proportional to incident light intensity) for a different pixel of what will eventually become a digital image, and an encoder (for example included in controller 121) interprets each of these voltages and assigns a value to each that is proportional to the voltage. One such embodiment of X-ray sensor panel 127 is illustrated in FIG. 2.

Figure 2:
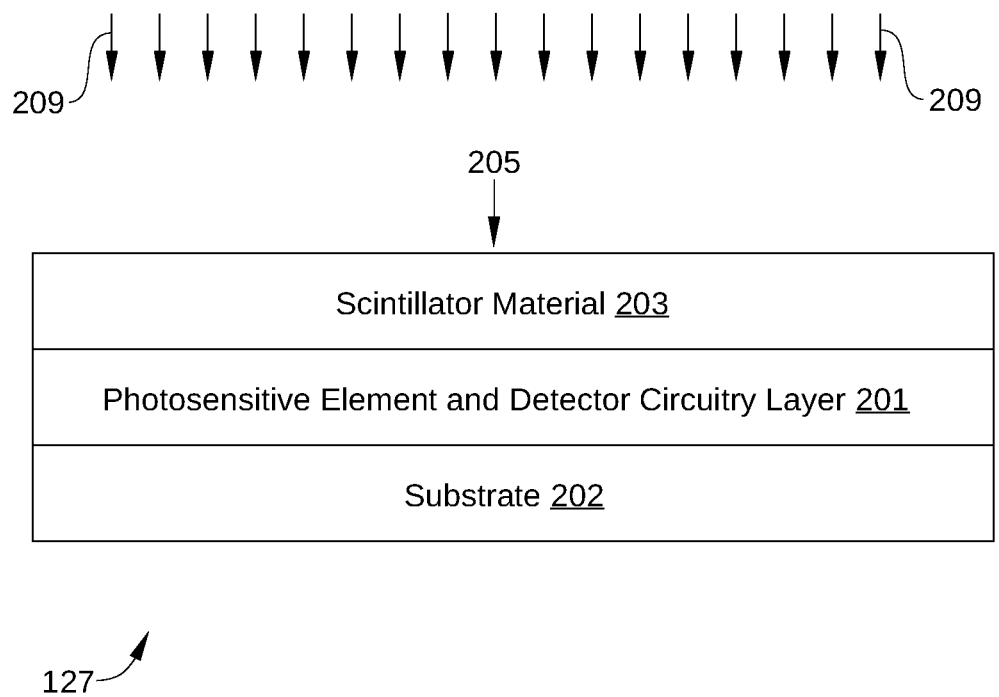
FIG. 2 schematically illustrates a cross-sectional view of an X-ray sensor panel, according to one embodiment of the disclosure.

FIG. 2 schematically illustrates a cross-sectional view of X-ray sensor panel 127, according to one embodiment of the disclosure. As shown, X-ray sensor panel 127 includes a photosensitive element and detector circuitry layer 201 formed on a substrate 202 and a layer of scintillator material 203 formed on photosensitive element and detector circuitry layer 201. Also shown are incident X-rays 209 that have passed through a patient, sample, or other object of interest after being generated by X-ray source 110. Together, photosensitive element and detector circuitry layer 201, substrate 202, and scintillator material 203 form an X-ray imaging matrix 205. It is noted that photosensitive element and detector circuitry layer 201 is generally formed from a plurality of processing layers, and that X-ray imaging matrix 205 may include additional material layers not illustrated in FIG. 2.

Photosensitive element and detector circuitry layer 201 generally includes a plurality of photosensitive elements, such as photodiodes, photogates, phototransistors, or any other suitable circuitry suitable for operation as pixel detector elements in X-ray sensor panel 127. For example, photosensitive element and detector circuitry layer 201 may also include thin-film transistors (TFTs) for reading out the digital signals from the pixel detector elements. Scintillator material 203 may include one or more material layers including, but no limited to, gadolinium oxisulfide ($Gd_2O_2S$:Tb), cadmium tungstate ($CdWO_4$), bismuth germanate ($Bi_4Ge_3O_{12}$ or BGO), cesium iodide (CsI), or cesium iodide thallium (CsI:Tl)), among others.

In the embodiment illustrated in FIG. 2, X-ray sensor panel 127 is depicted as an indirect flat panel detector, in which X-ray photons are converted to other light photons that are in turn detected and converted into charge. In other embodiments, X-ray sensor panel 127 can be a direct flat panel detector. In a direct FPD, incident X-ray photons are converted directly into charge in an amorphous selenium layer, and the resultant charge pattern therein is read out by suitable hardware, such as a thin-film transistor (TFT) array, an active matrix array, microplasma line addressing, or the like.

Returning to FIG. 1, in some embodiments, X-ray detector 120 includes one or more feedback indicators 128 configured to provide feedback to a user regarding the current status of X-ray detector 120. Feedback indicator(s) 128 can indicate power state, wireless connection state (i.e., whether X-ray detector 120 has successfully established wireless communications with workstation 130 after workstation tag 140 has been scanned), and whether X-ray detector 120 is ready to receive incident X-rays and acquire an X-ray image. Feedback indicators 128 can include one or more of a speaker, a light, a light emitting diode (LED), or a display screen. In some embodiments, feedback indicators 128 includes a controllable RGB LED that emits a light that matches the color associated with the workstation 130 for which X-ray detector 120 is currently configured for use. For example, when X-ray detector 120 has been successfully reconfigured for use with the workstation 130 associated with a blue workstation tag 140, feedback indicators 128 emit light that matches the blue color of that workstation tag 140. Alternatively, feedback indicators 128 can include a separate LED or other light-emitting indicator that each corresponds to a different possible workstation 130 for which X-ray detector 120 can be configured for use. In embodiments in which each workstation 130 is associated with a color group, feedback indicators 128 can include multiple such RGB LEDs that together emit a color group that matches the color group associated with the workstation 130 for which X-ray detector 120 is currently configured.

In some embodiments, X-ray detector 120 includes Hall effect sensor 129. Hall effect sensor 129 is configured to generate a reading of magnetic flux density, and therefore can be employed to detect when color sensor 122 is positioned proximate a magnet 142 in workstation tag 140. In such embodiments, Hall effect sensor 129 is configured to transmit a magnet detection signal to controller 121, which can, in response, activate color sensor 122. In some embodiments, the magnet detection signal can be the currently measured value of magnetic flux density, and logic within controller 121 determines whether Hall effect sensor 129 is proximate a workstation tag 140 based on that value. Alternatively, Hall effect sensor 129 includes such logic, and the magnetic detection signal is a binary signal indicating that Hall effect sensor 129 is either proximate a workstation tag 140 or is not proximate a workstation tag 140.

Because Hall effect sensor 129 is generally a very low power consumption device, Hall effect sensor 129 can remain continuously on during use of FP 120 without significantly affecting battery life. By contrast, color sensor 122 and any associated white light source is generally a higher power consumption device, and remains off until Hall effect sensor 129 detects workstation tag 140. Thus, by maintaining color sensor 122 in an inactive state except when an activation signal is received, power use by X-ray detector 120 can be significantly reduced and false color readings by color sensor 122 can be avoided.

Alternatively or additionally, X-ray detector 120 can include a mechanical user input device (not shown), such as a button or switch, to generate an activation signal indicating that color sensor 122 can be activated. Thus, in such embodiments, when a user of X-ray detector 120 positions color sensor 122 of X-ray detector 120 proximate workstation tag 140, the user can actuate the mechanical user input device to activate color sensor 122.

Workstation 130 may be any technically feasible computing device that includes a display device for displaying a UI and is capable of wirelessly connecting to X-ray detector 120. For example, in some embodiments, workstation 130 may be desktop or laptop computer that is configured to interact with (e.g., receive output from and provide input to) X-ray detector 120. In other embodiments, workstation 130 may be a mobile computing device, such as a smartphone, a wearable computing device, or an electronic tablet. In either case, workstation 130 includes a wireless module 132 that can be similar in functionality to wireless module 124 of X-ray detector 120. In some embodiments, workstation 130 is programmed with an FPD control application 131 that enables user interactions with X-ray detector 120.

In addition, in some embodiments, workstation 130 is programmed with an image processing application 133 for processing image data received from X-ray detector 120. Image processing application 133 may be configured to convert a digital representation or other image data into a digital image in a specific image file format and/or to modify the resultant digital image. Thus, once a digital representation is received from X-ray detector 120, image generation and post-processing can be performed independently from the operation of X-ray detector 120. For example, image processing application 133 may provide image processing capability for radiographic (still-picture X-ray) applications and/or fluoroscopic (video X-ray) applications.

Workstation 130 may be further configured to query, over a network, a list of patients and studies to be performed, such as a Digital Image and Communications in Medicine (DICOM) Modality Worklist Server or other remote server; to locally store a list of patients and studies to be performed, similar to a DICOM Modality Worklist Server; to provide a user interface to access a locally stored patient/study list; to maintain a local record of studies performed and images acquired, such as a panel-resident version of a DICOM picture archiving and communication system (PACS); to provide a user interface to view and/or review such studies; and to transmit studies performed, including images, directly to one or more remote servers (not shown). One embodiment of workstation 130 is illustrated in FIG. 3.

Figure 3:
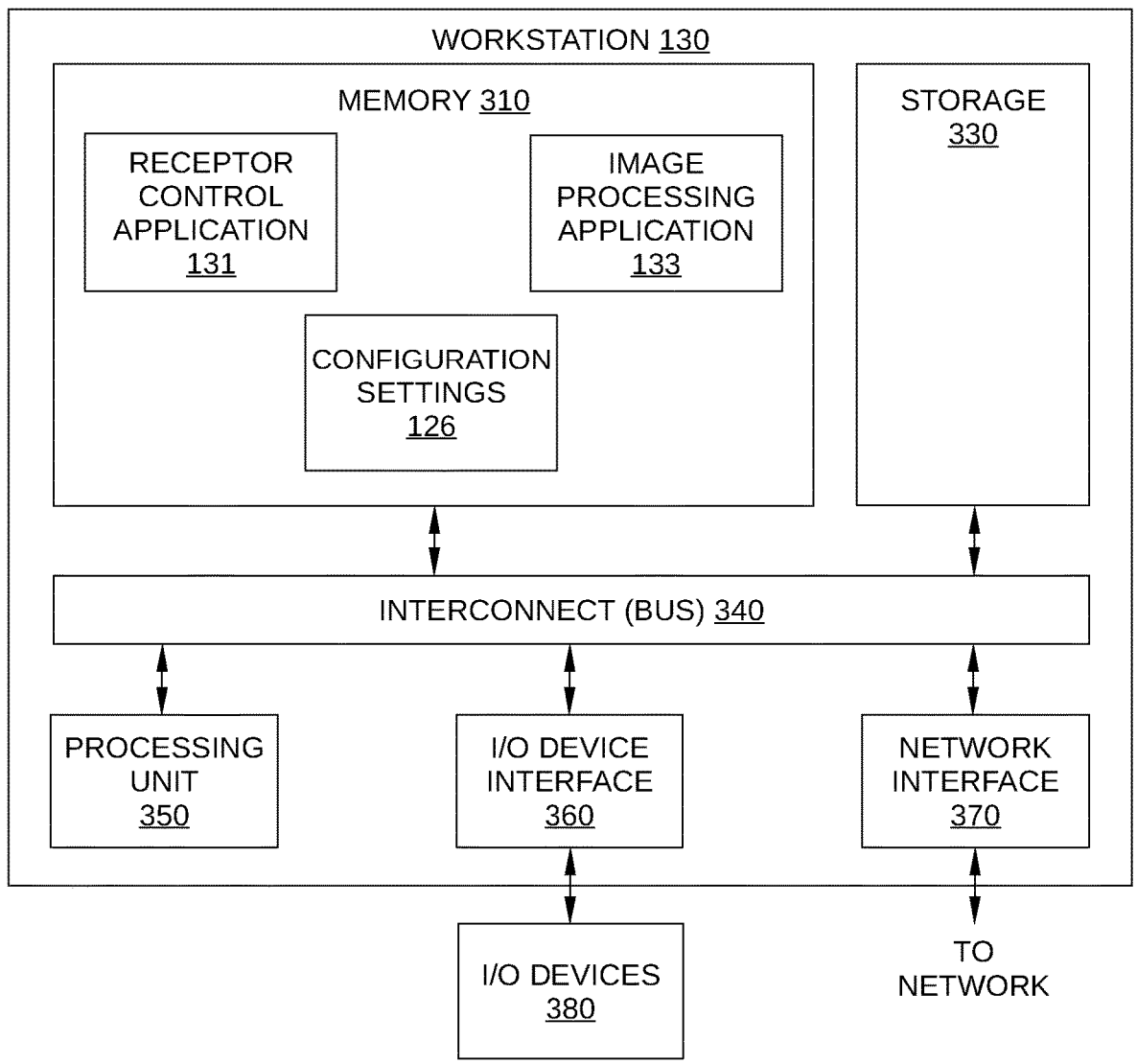
FIG. 3 is an illustration of a workstation in the digital radiographic system of FIG. 1, according to various embodiments of the present invention.

FIG. 3 is an illustration of workstation 130, according to various embodiments of the present invention. As noted, workstation 130 may be a desktop computer, a laptop computer, a smart phone, or any other type of computing device suitable for practicing one or more embodiments of the present invention. In operation, workstation 130 is configured to execute receptor control application 131 and/or image processing application 133, as described herein. It is noted that the computing device described herein is illustrative and that any other technically feasible configurations fall within the scope of the present invention.

As shown, workstation 130 includes, without limitation, an interconnect (bus) 340 that connects a processing unit 350, an input/output (I/O) device interface 360 coupled to input/output (I/O) devices 380, memory 310, a storage 330, and a network interface 370. Processing unit 350 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 350 may be any technically feasible hardware unit capable of processing data and/or executing software applications, including receptor control application 131, image processing application 133, and/or workstation configuration settings 126.

I/O devices 380 may include devices capable of providing input, such as a keyboard, a mouse, a touch-sensitive screen, and so forth, as well as devices capable of providing output, such as a display device and the like. Additionally, I/O devices 380 may include devices capable of both receiving input and providing output, such as a touchscreen, a universal serial bus (USB) port, and so forth. I/O devices 380 may be configured to receive various types of input from an end-user of workstation 130, and to also provide various types of output to the end-user of workstation 130, such as displayed digital images or digital videos. In some embodiments, one or more of I/O devices 380 are configured to couple workstation 130 to a network.

Memory 310 may include a random access memory (RAM) module, a flash memory unit, or any other type of memory unit or combination thereof. Processing unit 350, I/O device interface 360, and network interface 370 are configured to read data from and write data to memory 310. Memory 310 includes various software programs that can be executed by processor 350 and application data associated with said software programs, including receptor control application 131, image processing application 133, and/or workstation configuration settings 126.

Returning to FIG. 1, workstation tag 140 is associated with a single workstation 130, and includes color patch 141 and a magnet 142. Color patch 141 is a unique color that is included in color/ID mapping 125 and is mapped to the workstation 130 that is associated with workstation tag 140. Magnet 142 can be any technically feasible material or object that produces a magnetic field of suitable strength to be detected by Hall effect sensor 129 when within a target distance of Hall effect sensor 129. It is noted that minimizing or otherwise reducing the possibility of false color readings by color sensor 122 is generally beneficial for power conservation and for the uninterrupted operation of X-ray detector 120. Consequently, in some embodiments, magnet 142 is selected to have a magnetic field of a certain strength, and Hall effect sensor 129 is configured with a certain sensitivity, so that Hall effect sensor 129 does not detect magnet 142 unless within a relatively short distance, e.g., one to ten centimeters. In such embodiments, Hall effect sensor 129 is highly unlikely to falsely detect magnet 142 due to being held proximate some other magnet.

In some embodiments, workstation tag 140 is mounted on and/or disposed proximate the workstation 130 associated therewith. In such embodiments, a user of X-ray detector 120 can simply approach the associated workstation 130 while holding X-ray detector 120, position color sensor 122 of X-ray detector 120 proximate workstation tag 140, check for an indicator that confirms that X-ray detector 120 has been successfully reconfigured for use with that particular workstation 130, and position X-ray detector 120 as desired for X-ray image acquisition. Thus, the user of X-ray detector 120 is not required to enter any configuration information, or information that enables establishment of wireless communication between X-ray detector 120 and the workstation associated with workstation tag 140. As a result, in some embodiments, X-ray detector 120 includes no input devices for the inputting of data, such as an SSID of a workstation 130.

Figure 4:
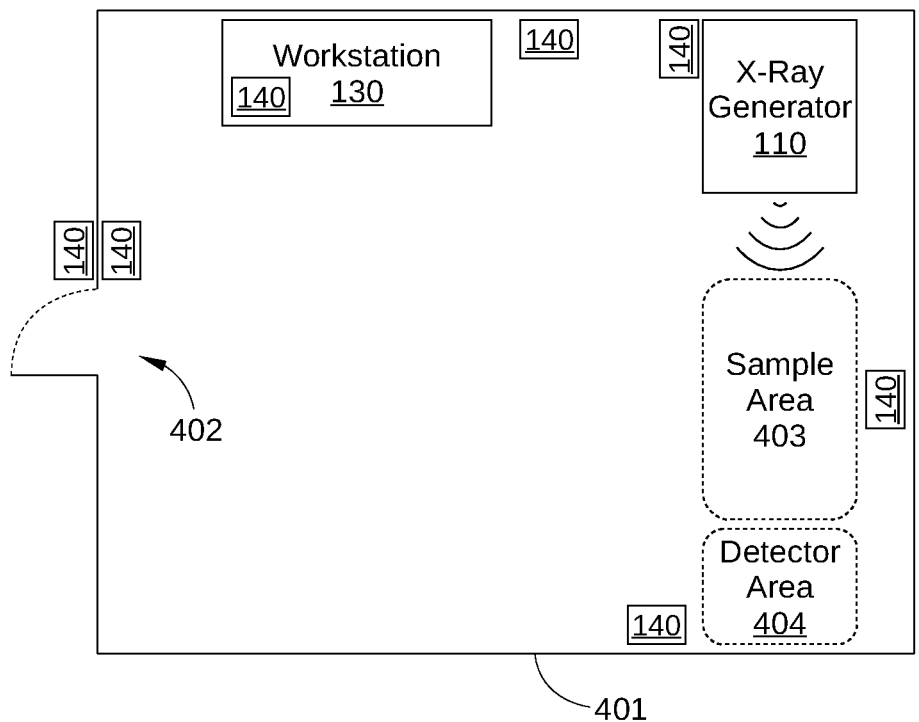
FIG. 4 schematically illustrates a room in a clinical environment, such as a hospital, according to one or more embodiments of the present disclosure.

In some embodiments, multiple similar workstation tags 140 are associated with a single workstation 130. In such embodiments, each of the similar workstation tags 140 have the same color, i.e., the color associated with that particular workstation 130, but are positioned at different locations that are each convenient for a user of X-ray detector 120 to access with color sensor 122 of X-ray detector 120. One such embodiment is illustrated in FIG. 4. FIG. 4 schematically illustrates a room 401 in a clinical environment, such as a hospital, according to one or more embodiments of the present disclosure. As shown, a workstation 130 and an X-ray source 110 are disposed within room 401, as well as a plurality of workstation tags 140. Each of the plurality of workstation tags 140 is disposed at a different location that provides convenient access to a user of X-ray detector 120. Specifically, in the embodiment illustrated in FIG. 4, a workstation tag is located immediately outside or inside an entrance 402 of room 401, on the workstation 130 located within room 401, proximate the workstation 130 located within room 401, on or adjacent to the X-ray source 110 located within room 401, proximate a sample area 403 (in which a sample, patient, or other object of interest is located during X-ray imaging), and/or proximate a detector area 404 (in which X-ray detector 120 is positioned during X-ray imaging). Thus, when a user of X-ray detector 120 enters room 401 with X-ray detector 120, the user can quickly access one of workstation tags 140, and thereby automatically reconfigure X-ray detector 120 for the workstation 130 located in room 401.

Figure 5:
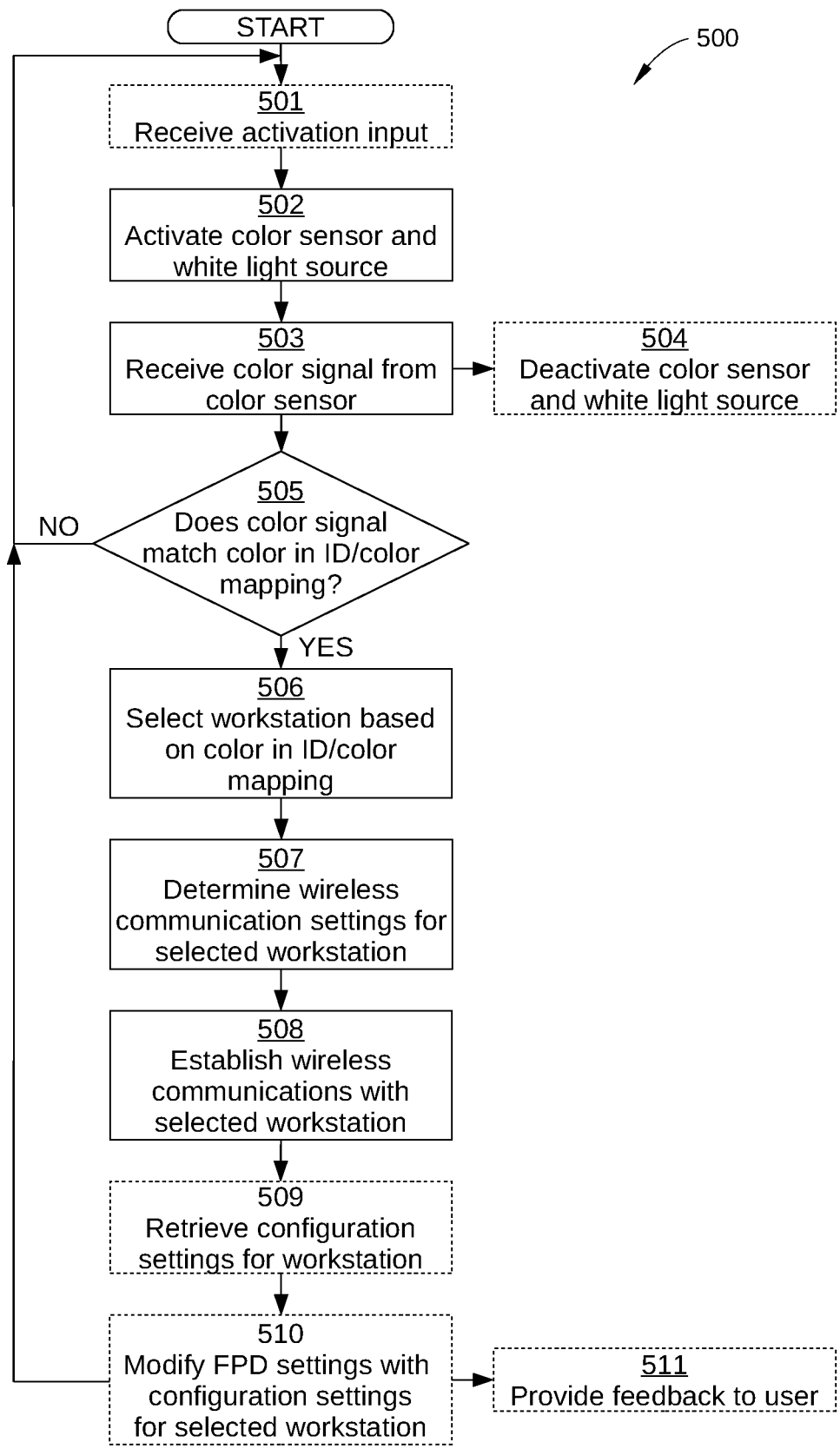
FIG. 5 sets forth a flowchart summarizing an example method for configuring an X- flat-panel detector for one of multiple image acquisition workstations, according to one or more embodiments of the present disclosure.

FIG. 5 sets forth a flowchart of an example method for configuring an X- flat-panel detector for one of multiple image acquisition workstations, according to one or more embodiments of the present disclosure. The method may include one or more operations, functions, or actions as illustrated by one or more of blocks 501-511. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with digital radiographic system 100 of FIGS. 1-4, persons skilled in the art will understand that any suitably configured radiographic system is within the scope of the invention.

Prior to the method steps, color/ID mapping 125 is input, programmed, or otherwise stored in X-ray detector 120. In some embodiments, color/ID mapping 125 is user-configurable, and can be modified as workstations 130 are added to or removed from the group of workstations shared by X-ray detector 120. In addition, configuration settings 126 are stored in X-ray detector 120 for one or more workstations 130 prior to the method steps. In some embodiments, the configuration settings 126 for a particular workstation 130 are entered or otherwise input at that workstation 130, and are then transferred to X-ray detector 120, via a wired or wireless connection. For example, the first time that X-ray detector 120 is used in conjunction with a particular workstation 130, the above procedure can be performed. Subsequently, X-ray detector 120 is configured for use by the particular workstation 130 via the method steps set forth below. In some embodiments, some or all of configuration settings 126 may also be stored in the associated workstation 130. In such embodiments, once a wireless communication connection is established between X-ray detector 120 and a workstation 130, configuration settings can be downloaded by X-ray detector 120 from the workstation 130.

A method 500 begins at optional step 501, in which controller 121 receives an activation input. In some embodiments, the activation input is a magnet detection signal from Hall effect sensor 129. Alternatively, the activation input is a magnetic flux reading that exceeds a predetermined threshold value. In either case, the activation input is generated by Hall effect sensor 129 when a user of X-ray detector 120 positions Hall effect sensor 129 proximate a workstation tag 140 that includes a suitable magnet 142. In some embodiments, Hall effect sensor 129 is located in X-ray detector 120 proximate color sensor 122. Consequently, in such embodiments, when Hall effect sensor 129 detects the presence of a magnet 142, color sensor 122 is typically directed toward the workstation tag 140 that includes the magnet 142. Alternatively or additionally, in embodiments in which X-ray detector 120 includes a mechanical user input device to generate an activation signal, such as a button or switch, the activation input received in step 501 can be a signal indicating that such a button has been depressed or switch has been actuated by a user of X-ray detector 120.

In step 502, controller 121 activates color sensor 122 for measuring a color. In embodiments in which color sensor 122 includes a white light source, controller 121 also activates the white light source, thereby illuminating workstation tag 140 with a substantially uniform spectrum of light.

In step 503, controller 121 receives a color signal from color sensor 122. In some embodiments, the color signal includes a specific identifier associated with the color detected by color sensor 122. Alternatively, the color signal includes the relative RGB values measured by color sensor 122, such as the 24-bit RGB values used in the RGB color system.

In optional step 504, after receiving the color signal from color sensor 122, controller 121 deactivates color sensor 122 and/or, when applicable, the white light associated therewith. In some embodiments, controller 121 deactivates color sensor 122 after a predetermined time interval has elapsed since color sensor 122 was activated. Additionally or alternatively, in some embodiments, controller 121 deactivates color sensor 122 after receiving a recognized color signal for a predetermined time interval, indicating that a user is holding color sensor 122 of X-ray detector 120 proximate a workstation tag 140.

In step 505, after receiving the color signal from color sensor 122, controller 121 determines whether the color signal matches a color included in ID/color mapping 125. If yes, method 500 proceeds to step 506; if no, the method proceeds back to the start of method 500.

In embodiments in which the color signal includes RGB values, controller 121 may determine that the color signal matches a color included in ID/color mapping 125 when the RGB values of the color signal are within a predetermined range of a color included in ID/color mapping 125. Thus, exact matching of the color signal and a color included in ID/color mapping may not be necessary.

In step 506, controller 121 selects a particular workstation 130 based on the color in ID/color matching 125 that matches the color signal received in 504 and on color/ID mapping 125.

In step 507, controller 121 determines wireless communication settings for the workstation 130 selected in step 506. Specifically, controller 122 looks up the wireless communications settings in configuration settings 126 that correspond to the workstation 130 selected in step 506.

In step 508, controller 121 establishes wireless communications with the workstation 130 selected in step 506, for example via wireless module 124 and the wireless communication settings determined in step 507. Alternatively, controller 121 initiates a request with the workstation 130 selected in step 506 for establishment of wireless communications, using the wireless communication settings determined in step 507.

In optional step 509, controller 121 retrieves one or more configuration settings 126 for the workstation 130 selected in step 506. As noted above, configuration settings 126 may include operational settings for X-ray detector 120 and/or software settings associated with the control or operation of X-ray detector 120.

In optional step 510, controller 121 modifies one or more operational settings of X-ray detector 120 with the one or more configuration settings retrieved in step 509 from configuration settings 126. Method 500 then proceeds back to the start of method 500. That is, X-ray detector 120 continues to operate using the configuration settings implemented in step 510 until another activation input is received by controller 121 and a color signal that matches a different color included in ID/color mapping 125 is detected by color sensor 122.

In optional step 511, controller 121 causes an appropriate feedback indicator 128 to provide feedback to the user indicating that X-ray detector 120 has established wireless communication with the workstation 130 selected in step 506 and has been reconfigured for use with the workstation 130 selected in step 506. In some embodiments, an RGB LED emits a light that matches the color included in ID/color mapping 125 that is associated with the workstation 130 selected in step 506. Alternatively or additionally, a sound may be emitted by X-ray detector 120 and/or an indicator light or LED in X-ray detector 120 may be energized that corresponds to the workstation 130 selected in step 506.

An X-ray flat-panel detector in a digital radiographic system can be automatically configured with settings for a specific image acquisition workstation, when the flat-panel detector is shared between multiple such workstations. A color sensor incorporated into the X-ray flat-panel detector is activated and then used to detect the color of a color-coded identification tag associated with the selected workstation. Based on the detected color, the X-ray flat-panel detector then changes one or more operational settings of the X-ray flat-panel detector, thereby enabling X-ray image acquisition via the selected workstation without inputs or other configuration changes being entered by the user.

Advantages of the disclosed embodiments described herein include the ability to automatically reconfigure an X-ray flat-panel detector for a different image acquisition workstation or other computing device by merely reading a color tag associated with the specific workstation via a color sensor incorporated into the X-ray flat-panel detector without the use of a cable, which can get lost, generate a tripping hazard, or have mechanical or electrical deterioration due to numerous insertions over time. An additional advantage is that power consumption by the color sensor can be minimized or otherwise reduced by maintaining the color sensor and any associated white light source in a deactivated state until a magnet detection signal (or other activation input signal) is received. The color sensor can consume less power and have greater reliability than bar code or laser readers. A further advantage is that after the initial configuration setup for a particular workstation, the X-ray flat-panel detector is configured for use with that particular workstation with no data inputs by a user, streamlining the reconfiguration process and avoiding data entry errors. Yet another advantage is that an X-ray flat-panel detector that includes a color sensor, a Hall effect sensor, and an RGB LED as a feedback indicator can readily conform to most solid and liquid ingress protection standards associated with the hospital environment. A further advantage is that an X-ray flat-panel detector that includes a color sensor does not require regulatory certification, as is needed for other non-standard wireless communication, such as NFC readers.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. An X-ray imaging device, comprising:
   a color sensor configured to generate a color signal indicating a particular color sensed;
   an imaging matrix of pixel detector elements that are each configured to detect photon energy and generate an image signal; and
   a controller that is coupled to the color sensor, the imaging matrix, and a wireless transceiver and is configured to:
   receive a color signal from the color sensor;
   determine an identifier of a computing device external to the X-ray imaging device based on the color signal; and
   change at least one operational setting of the X-ray imaging device based on the identifier.

2. The X-ray imaging device of claim 1, wherein the at least one operational setting of the imager includes one or more of a wireless communication setting for establishing a wireless communication connection with the computing device external to the X-ray imaging device, a software setting of an application running on the computing device external to the X-ray imaging device, enablement of an operating feature of the X-ray imaging device; and disablement of an operating feature of the X-ray imaging device.

3. The X-ray imaging device of claim 1, further comprising the wireless transceiver configured to transmit image data to a computing device external to the X-ray imaging device, wherein the controller is further configured to cause the wireless transceiver to establish a wireless communication connection with the computing device external to the X-ray imaging device based on the identifier.

4. The X-ray imaging device of claim 2, wherein the application running on the computing device external to the X-ray imaging device comprises an application for controlling operation of the imaging device.

5. The X-ray imaging device of claim 1, further comprising a Hall sensor coupled to the controller, and wherein the controller is further configured to activate the color sensor in response to receiving a magnet detection signal from the Hall sensor.

6. The X-ray imaging device of claim 1, further comprising a physical input device, and wherein the controller is further configured to activate the color sensor in response to receiving a user physical interaction with the physical input device.

7. The X-ray imaging device of claim 1, wherein the at least one operational setting of the X-ray imaging device includes a wireless communication setting for establishing a wireless communication connection with the computing device external to the X-ray imaging device, and the controller is configured to change the at least one operational setting prior to causing the wireless transceiver to establish the wireless communication connection with the computing device external to the X-ray imaging device.

8. The X-ray imaging device of claim 1, wherein the controller is configured to restart the X-ray imaging device prior to causing the wireless transceiver to establish a wireless communication connection with the computing device external to the X-ray imaging device.

9. The X-ray imaging device of claim 1, wherein the controller determines the identifier of the computing device external to the X-ray imaging device based on the color signal via a mapping of one or more identifiers to respective computing devices that are each external to the X-ray imaging device.

10. The X-ray imaging device of claim 9, wherein each of the respective computing devices that are external to the X-ray imaging device is configured with an application for controlling operation of the X-ray imaging device.

11. The X-ray imaging device of claim 1, wherein the controller is further configured to generate image data based on the plurality of image signals from the pixel detectors.

12. The X-ray imaging device of claim 11, wherein the controller is further configured to cause the image data to be transmitted to the computing device external to the X-ray imaging device via the wireless transceiver.

13. A method of configuring an X-ray imaging device for use with a computing device external to the X-ray imaging device, the method comprising:
   activating a color sensor configured to generate a color signal indicating a particular color sensed;
   receiving the color signal from the color sensor;
   determining an identifier of the computing device external to the X-ray imaging device based on the color signal; and
   changing at least one operational setting of the X-ray imaging device based on the identifier.

14. The method of claim 13, wherein the at least one operational setting of the X-ray imaging device includes one or more of a wireless communication setting for establishing the wireless communication connection with the computing device external to the X-ray imaging device, a software setting of an application running on the computing device external to the X-ray imaging device, enablement of an operating feature of the X-ray imaging device; and disablement of an operating feature of the X-ray imaging device.

15. The method of claim 14, further comprising causing a wireless transceiver included in the X-ray imaging device to establish a wireless communication connection with the computing device external to the X-ray imaging device based on the identifier.

16. The method of claim 13, further comprising receiving a signal from a Hall sensor included in the X-ray imaging device indicating a magnet detection by the Hall sensor, wherein activating the color sensor comprises activating the color sensor in response to receiving the signal from the Hall sensor.

17. The method of claim 13, further comprising receiving a signal from a physical input device included in the X-ray imaging device indicating a user physical interaction with the physical input device, wherein activating the color sensor comprises activating the color sensor in response to receiving the signal from the Hall sensor.

18. The method of claim 13, wherein determining the identifier of the computing device external to the X-ray imaging device comprises determining the identifier of the computing device based on the color signal via a mapping of one or more identifiers to respective computing devices external to the X-ray imaging device.

19. The method of claim 13, further comprising:
after changing the at least one operational setting, receiving a plurality of image signals from an imaging matrix of pixel detector elements included in the X-ray imaging device that are each configured to detect photon energy and generate an image signal;
generating image data based on the plurality of image signals and on the at least one operation setting; and
causing the image data to be transmitted to the computing device external to the X-ray imaging device via a wireless transceiver included in the X-ray imaging device.

20. An X-ray imaging device, comprising:
a color sensing means configured to generate a color signal indicating a particular color sensed; and
a controlling means configured to:
activate the color sensing means;
receive the color signal from the color sensing means;
determine an identifier of a computing device external to the X-ray imaging device based on the color signal; and
change at least one operational setting of the X-ray imaging device based on the identifier.

* * * * *